(12) United States Patent
Ono

(10) Patent No.: US 9,889,444 B2
(45) Date of Patent: Feb. 13, 2018

(54) ANALYSIS TOOL AND MICROANALYSIS SYSTEM

(75) Inventor: Koichi Ono, Saitama (JP)

(73) Assignee: ENPLAS CORPORATION, Tokyo (JP)

( * ) Notice: Subject to any disclaimer, the term of this patent is extended or adjusted under 35 U.S.C. 154(b) by 376 days.

(21) Appl. No.: 13/811,466

(22) PCT Filed: Jul. 15, 2011

(86) PCT No.: PCT/JP2011/004054
§ 371 (c)(1),
(2), (4) Date: Jan. 22, 2013

(87) PCT Pub. No.: WO2012/011262
PCT Pub. Date: Jan. 26, 2012

(65) Prior Publication Data
US 2013/0121894 A1   May 16, 2013

(30) Foreign Application Priority Data
Jul. 22, 2010   (JP) .................................. 2010-165010

(51) Int. Cl.
*B01L 3/00*   (2006.01)
*G01N 21/05*   (2006.01)
(Continued)

(52) U.S. Cl.
CPC ............ *B01L 3/5027* (2013.01); *G01N 21/05* (2013.01); *G01N 21/645* (2013.01);
(Continued)

(58) Field of Classification Search
CPC ................................................ G01N 2021/058
(Continued)

(56) References Cited

U.S. PATENT DOCUMENTS 6,438,279 B1 *  8/2002  Craighead et al. ............. 385/12
7,379,178 B2 *  5/2008  Blair ...................... G01N 21/05
                                                    250/343
(Continued)

FOREIGN PATENT DOCUMENTS

JP      09-288090 A     11/1997
JP      2001-108618 A    4/2001
(Continued)

OTHER PUBLICATIONS

Seo et al., "Sensors and Actuators B" 99 (2004) 615-622, 8 pages.*
(Continued)

*Primary Examiner* — Bobby Ramdhanie
*Assistant Examiner* — Denise R Anderson
(74) *Attorney, Agent, or Firm* — Brundidge & Stanger, P.C.

(57) ABSTRACT

An analysis tool suppressing background and improving detection sensitivity. In a first plate is formed a first concavity having, in the path of excitation light of a surface opposite to a bonding surface, a first bottom surface, a first opening, and a slanted surface widening from the edge of the first bottom surface towards the edge of the first opening. In a second plate, having a flow path formed on the bonding surface, is formed a second concavity having, in the path of excitation light of the surface opposite to the bonding surface, a second bottom surface, a second opening, and a slanted surface widening from the edge of the second bottom surface towards the edge of the second opening. The first plate is bonded to the second plate, and the first opening and the second opening are covered with a film.

5 Claims, 8 Drawing Sheets

(51) Int. Cl.
*G01N 21/64* (2006.01)
*G01N 21/03* (2006.01)

(52) U.S. Cl.
CPC .................. *B01L 2300/0654* (2013.01); *B01L 2300/0816* (2013.01); *B01L 2300/0877* (2013.01); *B01L 2300/0887* (2013.01); *G01N 2021/0346* (2013.01); *G01N 2021/058* (2013.01)

(58) Field of Classification Search
USPC ........................................................ 422/503
See application file for complete search history.

(56) References Cited

U.S. PATENT DOCUMENTS

| | | |
|---|---|---|
| 2002/0005354 A1* | 1/2002 | Spence et al. ................ 204/450 |
| 2004/0069639 A1 | 4/2004 | Ono |
| 2005/0140971 A1 | 6/2005 | Yamaguchi et al. |
| 2008/0245971 A1* | 10/2008 | Wimberger-Friedl et al. ......................... 250/458.1 |
| 2009/0051912 A1* | 2/2009 | Salazar et al. ................ 356/246 |
| 2009/0155832 A1* | 6/2009 | Lo et al. ......................... 435/29 |
| 2010/0117224 A1* | 5/2010 | McElrea ................ H01L 24/24 257/723 |
| 2011/0134420 A1 | 6/2011 | Matsumoto et al. |

FOREIGN PATENT DOCUMENTS

| | | | | |
|---|---|---|---|---|
| JP | 2002-350333 | A | | 12/2002 |
| JP | 2003-279471 | A | | 10/2003 |
| JP | 2004-138411 | A | | 5/2004 |
| JP | 2007-298474 | A | | 11/2007 |
| JP | 2009-041984 | A | | 2/2009 |
| JP | 2009041984 | A | * | 2/2009 ............. G01N 21/03 |
| JP | 2009-063436 | A | | 3/2009 |
| WO | 2010/010904 | A1 | | 1/2010 |

OTHER PUBLICATIONS

Sia et al., "Electrophoresis" 24 (2003) 3563-3576, 14 pages.*
Fujimoto et al., JP2009041984 (A), Feb. 26, 2009, Abstract, Patent Publication, and Machine Translation, 54 pages.*

* cited by examiner

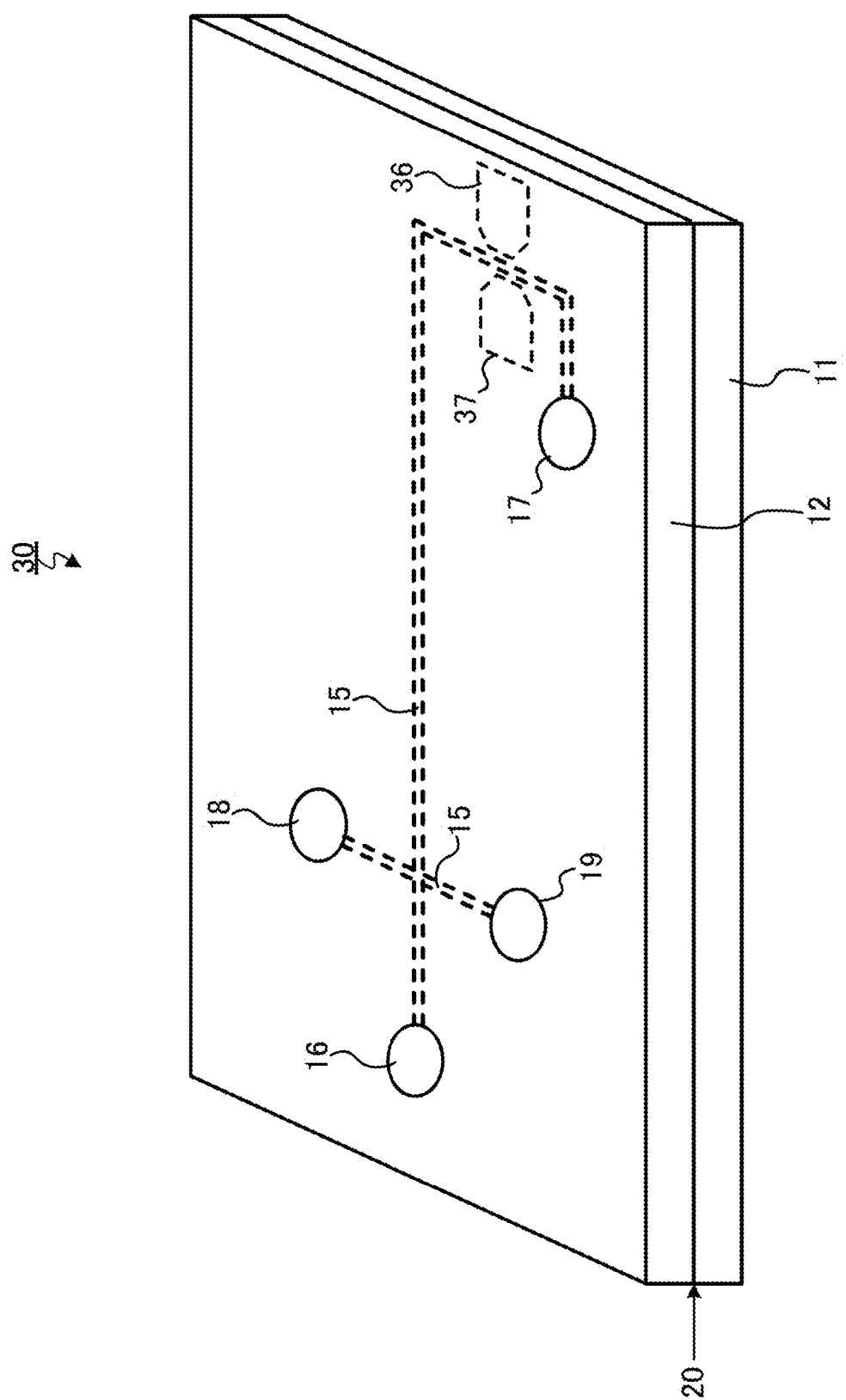

ANALYSIS TOOL AND MICROANALYSIS SYSTEM

TECHNICAL FIELD

The present invention relates to an analysis tool including a resin micro flow path chip and a micro analysis system including the analysis tool.

BACKGROUND ART

In a current scientific field or medical field such as biochemistry and analytical chemistry, a micro analysis system is employed for rapidly testing and analyzing a small amount of substances such as protein or nucleic acid (for example, DNA) with accuracy.

One of the micro analysis systems involves providing a micro flow path (hereinafter, referred to as "a flow path") having a width and a depth of approximately several tens to two hundreds μm in the interior of the analysis tool, filling electrophoretic solution (i.e., buffer solution, gel) in the flow path, infusing samples from the end of the flow path and applying a voltage to the solution, and applying an electrophoresis to the samples to analyze the samples.

In such a sample analysis, there is a known method of setting an analysis tool including a micro flow path in an analysis apparatus including an optical system unit capable of irradiating and receiving analysis light, applying electrophoresis to samples, irradiating light at a predetermined position in a flow path, and observing a fluorescence wavelength irradiated from the samples in the flow path, (see, for example, Patent literature 1).

CITATION LIST

Patent Literature

PLT 1
Japanese Patent Application Laid-Open No. 9-288090

SUMMARY OF INVENTION

Technical Problem

However, in the technique disclosed in the above described Patent literature 1, thick resin (substrate) in the path of light incident on the samples irradiates strong autofluorescence to increase background, which causes a problem of decreasing sample detection sensitivity.

When fibers, human skins, floaters in air and the like (hereinafter, referred to as "dust") are attached to the surface of resin (substrate) in the light path, and the distance between the dust and the focus of radiation light in the flow path is short, fluorescence irradiated from the dust is likely to be detected as noise and background is increased, thereby causing a problem of decreasing sample detection sensitivity.

It is an object of the present invention to provide an analysis tool and a micro analysis system which reduce background and improve sample detection sensitivity.

Solution to Problem

An analysis tool according to the present invention is an analysis tool configured by joining a first planar plate and a second planar plate, and employs a configuration in which the second plate has a flow path on a joint surface; and a pair of sealed spaces is located, across the flow path, in a path of excitation light incident on a sample at a predetermined position in the flow path and/or detection light from the sample irradiated with the excitation light, in a state in which the first plate and the second plate are joined.

The micro analysis system according to the present invention employs a configuration to include the above described analysis tool.

Advantageous Effects of Invention

According to the present invention, it is possible to reduce background and improve sample detection sensitivity.

BRIEF DESCRIPTION OF DRAWINGS

FIG. 5 is a perspective view showing the shape of an analysis tool according to Embodiment 2 of the present invention;

DESCRIPTION OF EMBODIMENTS

Embodiments of the present invention will now be described in detail with reference to the drawings.

Embodiment 1

Figure 1:
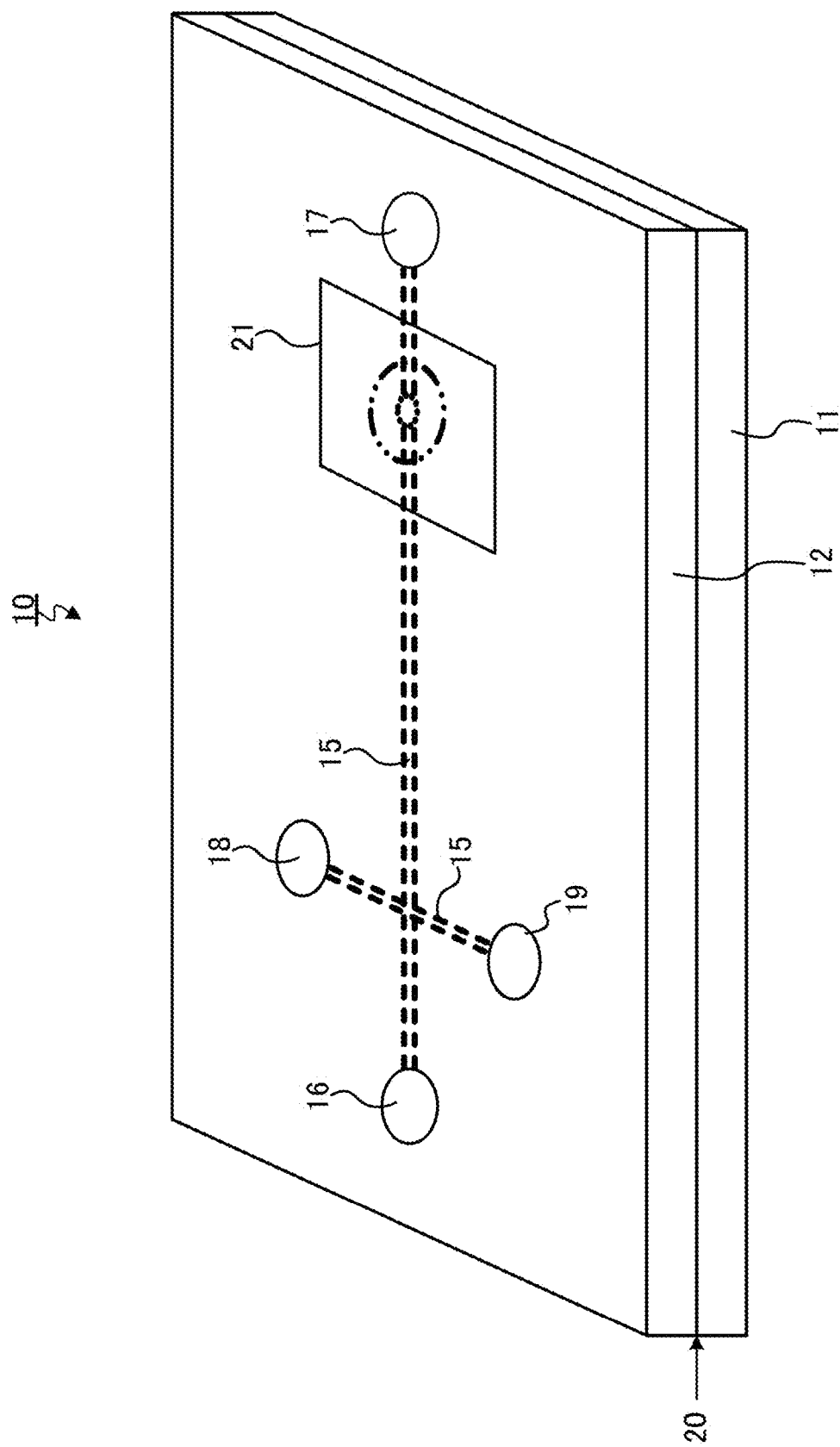
FIG. 1 is a perspective view showing the shape of an analysis tool according to Embodiment 1 of the present invention.

FIG. 1 is a perspective view showing the shape of analysis tool 10 according to Embodiment 1 of the present invention. As shown in FIG. 1, analysis tool 10 is configured by joining resin planar first plate 11 to second plate 12.

First plate 11 and second plate 12 are made of resin material having high light-permeability such as acryl, polycarbonate, and polyolefin, and are desirably made of the same materials.

First plate 11 has first recessed part 13 (see FIG. 2) in the path of excitation light incident on samples in later described flow path 15. Second plate 12 has cross-shaped groove 15', and when second plate 12 is joined to later described first plate 11, joint surface 20 of first plate 11 closes an opening of groove 15' to define flow path 15 for flowing samples. Second plate 12 further has ports 16 to 19 to fill each end of flow path 15 with samples and electrophoretic solution, and second recessed part 14 (see FIG. 3) in the path of radiation light (excitation light) to the samples.

First plate 11 is joined to second plate 12, for example, through adhesion with an organic adhesive or thermal compression bond.

Figure 2:
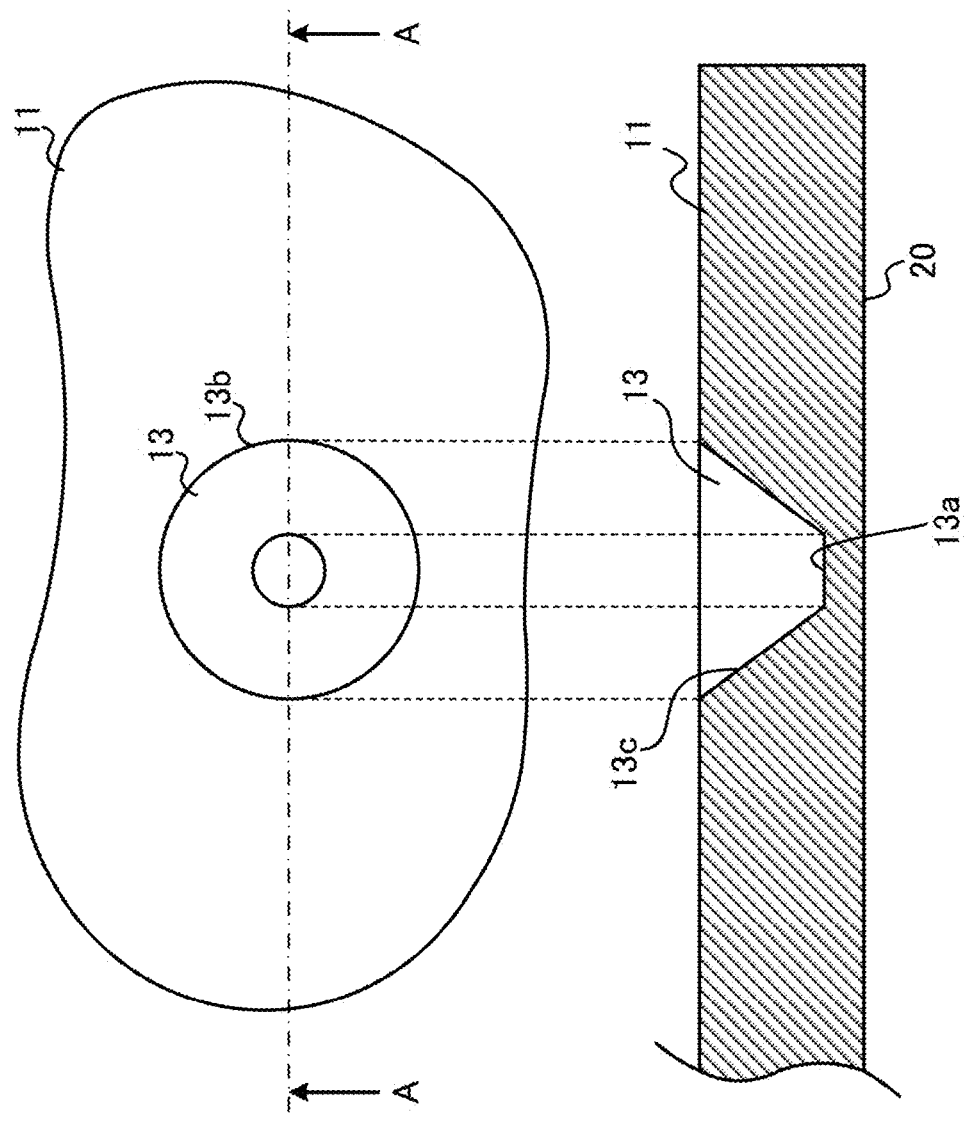
FIG. 2A is a bottom view including the first recessed part in the first plate shown in FIG. 1.
FIG. 2B is a cross-section view taken by line A-A in FIG. 2A.

FIG. 2A is a bottom view including first recessed part 13 in first plate 11. FIG. 2B is a cross-section view taken by line A-A in FIG. 2A. First plate 11 has first recessed part 13 on a surface opposite to joint surface 20 to second plate 12, as shown in FIG. 2. First recessed part 13 has a bottom surface (first bottom surface 13a), an opening (first opening 13b) and an inclined surface (first inclined surface 13c) (the surface of a tapered cylinder) expanding from the outer edge of first bottom surface 13a toward the opening edge of first opening 13b.

Figure 3:
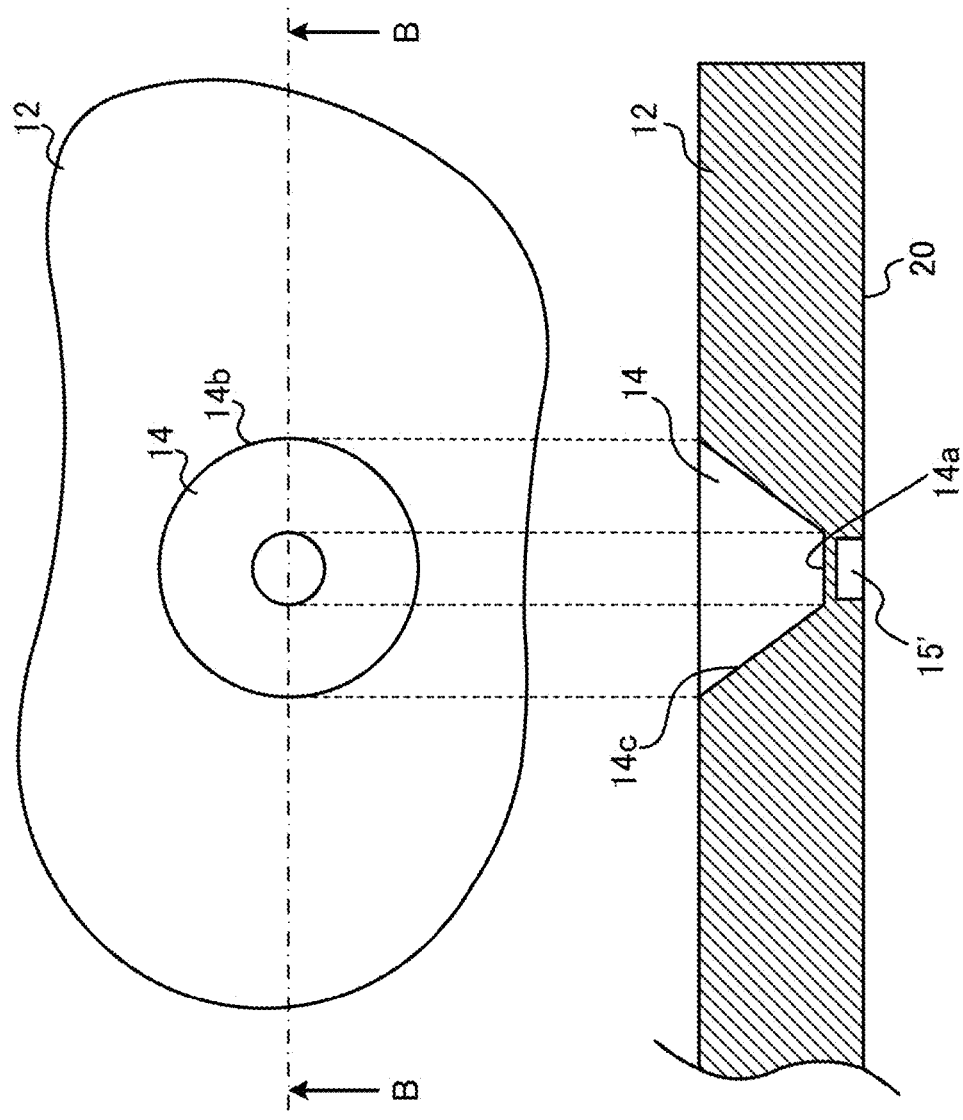
FIG. 3A is a plane view including the second recessed part in the second plate in FIG. 1.
FIG. 3B is a cross-section view taken by line B-B in FIG. 3A.

FIG. 3A is a plane view including second recessed part 14 in second plate 12. FIG. 3B is a cross-section view taken by line B-B in FIG. 3A. As shown in FIG. 3, second plate 12 has flow path 15 on joint surface 20 to first plate 11, and has second recessed part 14 on a surface opposite to joint surface 20 to first plate 11. Second recessed part 14 has a bottom surface (second bottom surface 14a), an opening (second opening 14b), and an inclined surface (second inclined surface 14c) (the surface of a tapered cylinder) expanding from the outer edge of second bottom surface 14a toward the opening edge of second opening 14b as with first recessed part 13.

In view of the above, providing a space with a plate being present in a path of excitation light by providing recessed parts in first plate 11 and second plate 12 can reduce the volume of resin, thereby minimizing the amount of autofluorescence irradiated with excitation light in a plate. Accordingly, the background can be minimized.

The cross section areas of recessed parts 13 and 14 respectively provided in first plate 11 and second plate 12 are defined so as to be larger as the cross sections of the recessed parts are close to openings 13b and 14b, which can readily shape first plate 11 and second plate 12.

Figure 4:
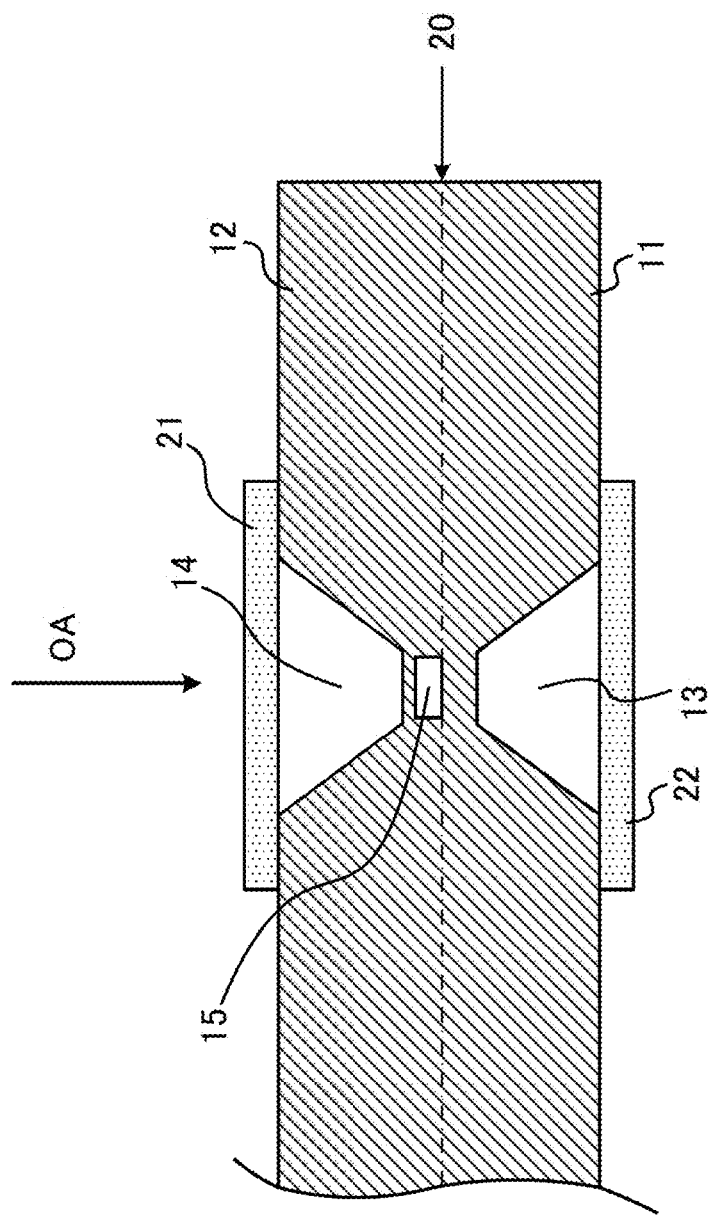
FIG. 4 is a cross-section view including the first recessed part, the second recessed part and a flow path in a joined first plate and second plate.

FIG. 4 is a cross-section view including first recessed part 13, second recessed part 14, and flow path 15 in joined first plate 11 and second plate 12. Closing groove 15' by joint surface 20 of first plate 11 defines flow path 15.

Opening 13b of first recessed part 13 provided in first plate 11 and opening 14b of second recessed part 14 provided in second plate 12 are respectively covered with films 21 and 22. Films having minimized thicknesses are selected for films 21 and 22 not so as to increase the amount of autofluorescence in the path of excitation light. This allows each of recessed parts 13 and 14 to be sealed space and blocks ingress of dust into each of recessed parts 13 and 14. Consequently, dust attached to the surface of analysis tool 10 is as away from a focus position as possible and an effect of fluorescence from dust irradiated with excitation light on detection sensitivity is reduced, thereby minimizing background.

According to the present embodiment, the excitation light is entered such that the direction of an optical axis (OA) is vertical to the plane surfaces of plates 11 and 12 (for example, joint surface 20) as shown in FIG. 4. Samples labeled with a fluorescence reagent or the like in flow path 15 receive the excitation light and irradiate detection light such as fluorescence, the detection light being detected in a light receiving section (not shown). When the excitation light and the detection light have the same optical axis, the detection light is directed to the light receiving section through first recessed part 13 or second recessed part 14.

According to Embodiment 1, the first plate having the first recessed part in the path of excitation light is joined to the second plate having the flow path for flowing samples and the second recessed part at a position irradiated with the excitation light. This can reduce the volume of resin being present in the path of the excitation light, thereby minimizing the amount of autofluorescence from the resin irradiated with the excitation light.

Covering each of openings in the first recessed part and the second recessed part with a film can block ingress of dust into each of recessed parts. Additionally, a surface on which dust is apt to be attached can be away from the focus of excitation light in the flow path. This can reduce an effect of fluorescence from dust irradiated with excitation light, on detection sensitivity.

As a result, it is possible to minimize background and improve sample detection sensitivity.

Embodiment 2

A case has been described where the excitation light is entered vertically to the surface of the plate in Embodiment 1. A case will be described where the excitation light is entered horizontally to the surface of the plate, in other words, entered from the side of the plate in Embodiment 2 of the present invention.

FIG. 5 is a perspective view showing the shape of analysis tool 30 according to Embodiment 2 of the present invention. As shown in FIG. 5, analysis tool 30 has sealed spaces 36 and 37 defined by joining first plate 11 to second plate 12.

Figure 6A:
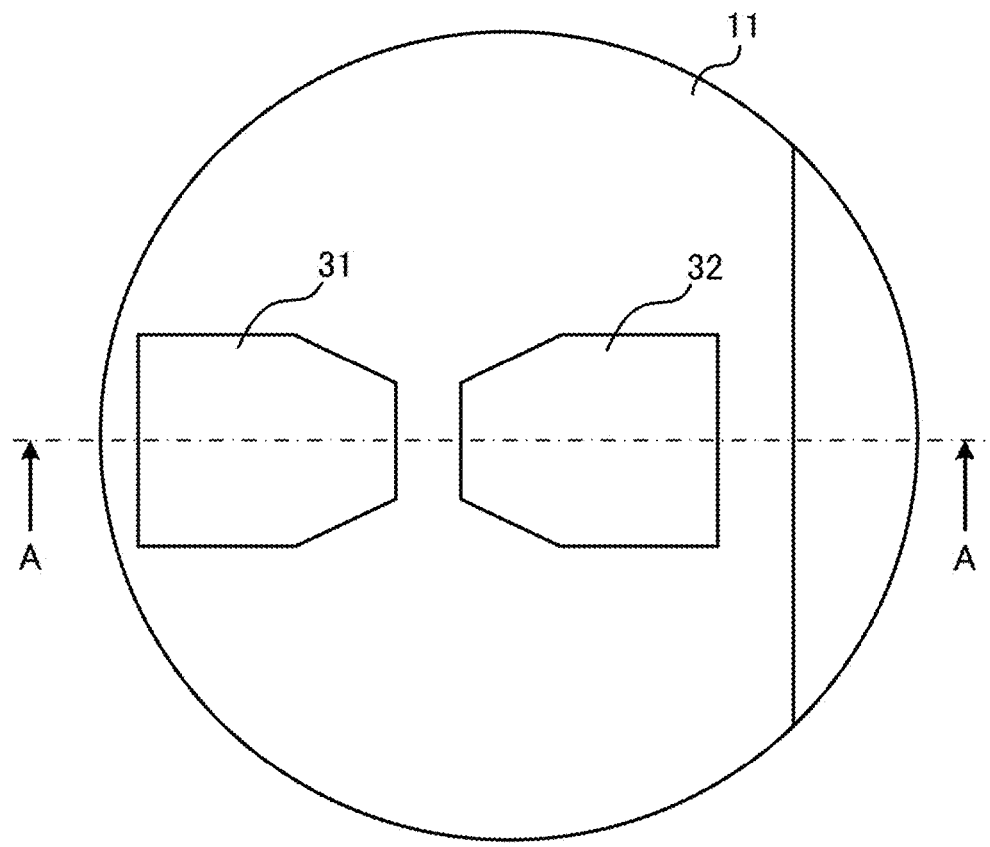
FIG. 6A is a plane view including the first recessed part and the second recessed part in the first plate in FIG. 5.
Figure 6B:
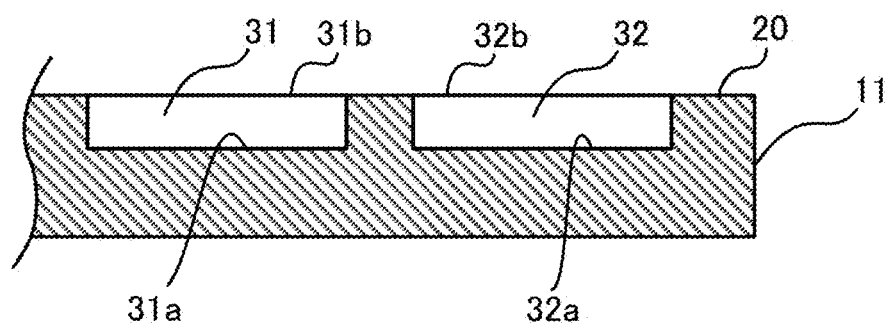
FIG. 6B is a cross-section view taken by line A-A in FIG. 6A.

FIG. 6A is a plane view including first recessed part 31 and second recessed part 32 in first plate 11 in FIG. 5, and FIG. 6B is a cross-section view taken by line A-A in FIG. 6A. As shown in FIG. 6, first plate 11 has first recessed part 31 having first opening 31b and second recessed part 32 having second opening 32b, on joint surface 20 to second plate 12 in the path of excitation light. First recessed part 31 and second recessed part 32 are shallow prismatic concaves having hexagonal bottom surfaces (first bottom surface 31a and second bottom surface 32a).

Figure 7A:
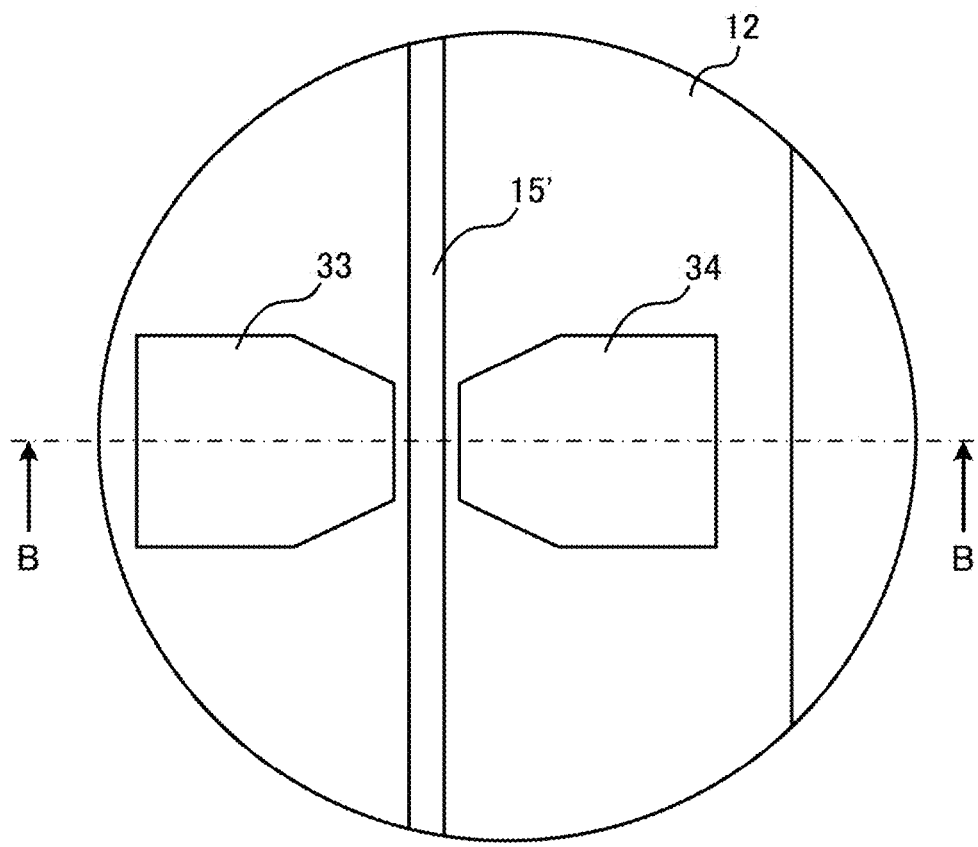
FIG. 7A is a bottom view including the third recessed part and the fourth recessed part in the second plate in FIG. 5.
Figure 7B:
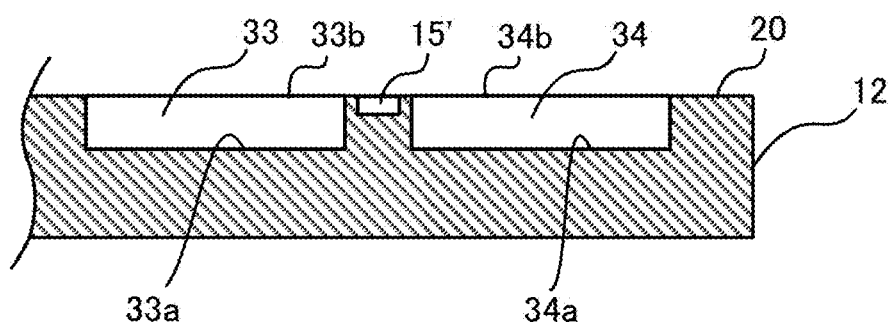
FIG. 7B is a cross-section view taken by line B-B in FIG. 7A.

FIG. 7A is a bottom view including third recessed part 33 and fourth recessed part 34 in second plate 12, and FIG. 7B is a cross-section view taken by line B-B in FIG. 7A. As shown in FIG. 7, second plate 12 has third recessed part 33 and fourth recessed part 34 on joint surface 20 to first plate 11 across groove 15'. Third recessed part 33 and fourth recessed part 34 are shallow prismatic concaves having openings (third opening 33b and fourth opening 34b) on joint surface 20 and hexagonal bottom surfaces (third bottom surface 33a and fourth bottom surface 34a), as with first recessed part 31 and second recessed part 32.

Figure 8:
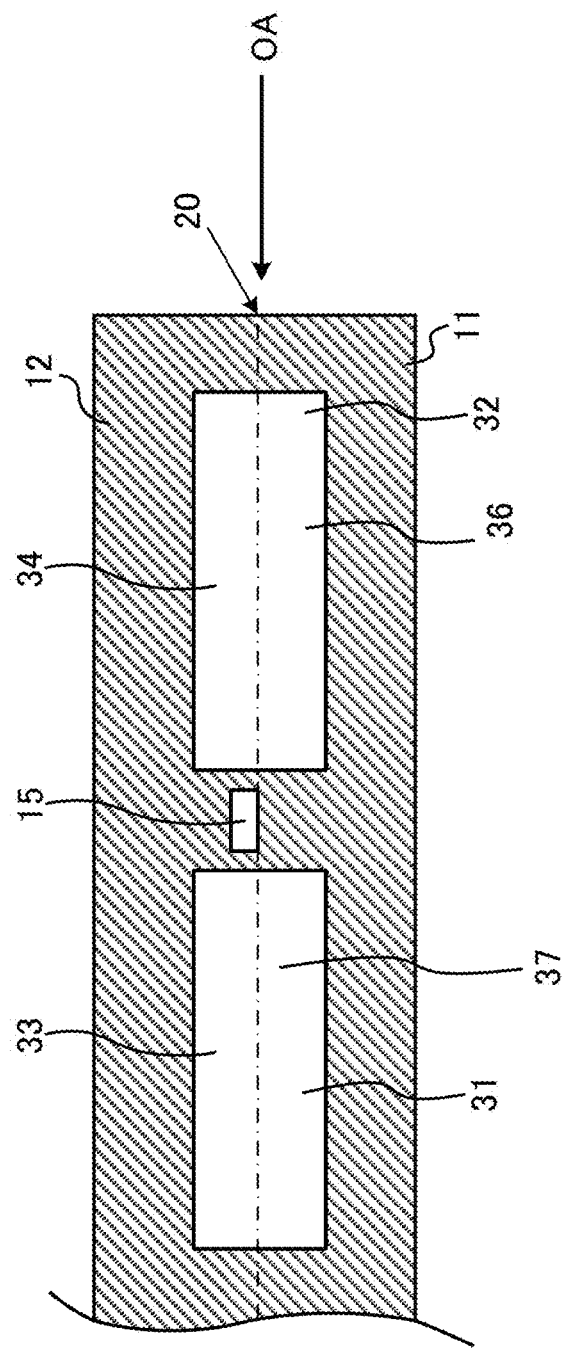
FIG. 8 is a cross-section view including the first to fourth recessed parts, and a flow path in joined first plate 11 and second plate 12.

FIG. 8 is a cross-section view including first to fourth recessed parts 31 to 34 and flow path 15 in joined first plate 11 and second plate 12. Joining first plate 11 to second plate 12 allows the opening of first recessed part 31 and the opening of second recessed part 32 of first plate 11 to respectively face the opening of third recessed part 33 and the opening of fourth recessed part 34 of second plate 12, thereby defining sealed spaces 36 and 37. The opening of groove 15' is closed by joint surface 20 of first plate 11 to define flow path 15.

The excitation light is entered such that the direction of an optical axis (OA) is horizontal to the plane surfaces of plates 11 and 12 (for example, joint surface 20) as shown in FIG. 8. Samples labeled with a fluorescence reagent or the like in flow path 15 receive the excitation light and irradiate detection light such as fluorescence, the detection light being detected in a light receiving section (not shown). When the excitation light and the detection light have the same optical axis, the detection light is directed to the light receiving section through sealed space 36 or 37.

According to Embodiment 2, the first plate having the first recessed part and the second recessed part at a position irradiated with excitation light is joined to the second plate having the flow path for flowing samples and the third recessed part and the fourth recessed part at a position irradiated with excitation light, across the flow path. The opening of the first recessed part and the opening of the second recessed part of the first plate respectively face the opening of the third recessed part and the opening of the fourth recessed part of the second plate, thereby defining sealed spaces. This can reduce the volume of resin being present in the path of excitation light, thereby minimizing the amount of autofluorescence from the resin irradiated with the excitation light, and can block ingress of dust into each recessed part, thereby reducing an effect of fluorescence from dust irradiated with excitation light, on detection sensitivity. Accordingly, it is possible to minimize background and improve sample detection sensitivity.

Analysis tool 30 according to Embodiment 2 may have all of the first to fourth recessed parts 31 to 34 and groove 15' on joint surface 20, and the depth of the concaves from joint surface 20 can be reduced (shallowed) in comparison with Embodiment 1. This can simplify a mold structure and allow assembling to be easy.

In the analysis tool, an effect of improving detection sensitivity according to the present invention can be obtained if a pair of sealed spaces across a flow path is located in the light path of at least one of an optical system for radiation of excitation light or the like and an optical system for detection of fluorescence or the like. A larger effect can however be obtained in a case where the pair of sealed spaces is defined in the light path of the optical system for radiation of excitation light. As with analysis tools 10 and 30 according to Embodiments 1 and 2, in a case where the optical system for radiation and the optical system for detection have the same optical axis, the present invention is further effective. When the optical system for radiation and the optical system for detection do not have the same axis (for example, a case where the axes of two optical systems are orthogonal to each other), a pair of sealed spaces across the flow path is desirably located in the light path of each optical system.

Embodiments 1 and 2 have described a flow path defined by closing a groove on the second plate with the first plate, but the present invention is not limited thereto, and the flow path may be defined by joining the openings of grooves in both the first plate and the second plate.

The shape of the pair of sealed spaces across the flow path is not limited to one shown in Embodiments 1 and 2. The pair of sealed spaces is desirably shaped such that the widths of the sealed spaces orthogonal to optical axes of the optical system for radiation and the optical system for detection are wide enough not to intercept light fluxes of each optical system, and a loss of light directed to a position irradiated with light (the focus of irradiated light) in a flow path and to a light receiving section for detection light can be minimized.

The pair of sealed spaces according to the present invention need only minimize the amount of autofluorescence and block ingress of dust, and need not have airtightness.

The disclosure of Japanese Patent Application No. 2010-165010 filed on Jul. 22, 2010, including the specification, drawings and abstract, is incorporated herein by reference in its entirety.

INDUSTRIAL APPLICABILITY

An analysis tool and a micro analysis system according to the present invention can be employed for an apparatus which tests and analyzes a small amount of substances in a scientific field or medical field such as biochemistry and analytical chemistry with accuracy.

REFERENCE SIGNS LIST 10, 30 Analysis tool
11 First plate
12 Second plate
13, 31 First recessed part
14, 32 Second recessed part
15 Flow path
16-19 Port
20 Joint surface
21, 22 Film
33 Third recessed part
34 Fourth recessed part
36, 37 Sealed space

The invention claimed is:

1. An analysis tool configured by joining a first planar plate and a second planar plate, wherein:
   the first planar plate and the second planar plate comprise a resin material having light permeability;
   the second planar plate has a flow path on a joint surface, wherein the flow path is covered by the first planar plate in a state in which the first planar plate and the second planar plate are joined;
   a pair of hermetically sealed spaces is located, across the flow path, in a path of excitation light incident on a sample at a predetermined position in the flow path and a path of detection light from the sample irradiated with the excitation light, in the state in which the first planar plate and the second planar plate are joined, the path of excitation light and the path of detection light being perpendicular to the joint surface and a flow direction of the flow path;
   the first planar plate has a first recessed part on a surface opposite to the joint surface;
   the second planar plate has a second recessed part on a surface opposite to the joint surface; and
   the pair of hermetically sealed spaces are defined by covering an opening of each of the first recessed part and the second recessed part with a film.

2. The analysis tool according to claim 1, wherein each of the first recessed part and the second recessed part has:
   a bottom surface;
   the opening located at the surface opposite to the joint surface; and
   an inclined surface that expands from an outer edge of the bottom surface toward the opening.

3. A micro analysis system comprising the analysis tool according to claim 1.

4. The analysis tool according to claim 1, wherein:
   each of the pair of hermetically sealed spaces is separated from the flow path.

5. The analysis tool according to claim 1, wherein:
the flow path is enclosed by the resin material in the state in which the first planar plate and the second planar plate are joined.

* * * * *